(12) United States Patent
Schnittger et al.

(10) Patent No.: US 6,387,947 B1
(45) Date of Patent: May 14, 2002

(54) ANTIMICROBIAL COSMETIC COMPOSITIONS

(75) Inventors: Steven F. Schnittger, Huntington Station, NY (US); Lieve Declercq, Ekeren (BE)

(73) Assignee: E-L Management Corp., New York, NY (US)

( * ) Notice: Subject to any disclaimer, the term of this patent is extended or adjusted under 35 U.S.C. 154(b) by 0 days.

(21) Appl. No.: 09/269,141

(22) PCT Filed: Jul. 15, 1998

(86) PCT No.: PCT/US98/14666

§ 371 Date: Aug. 23, 1999

§ 102(e) Date: Aug. 23, 1999

(87) PCT Pub. No.: WO99/03446

PCT Pub. Date: Jan. 28, 1999

Related U.S. Application Data

(60) Provisional application No. 08/896,194, filed on Jul. 17, 1997, now Pat. No. 6,114,377.

(51) Int. Cl.[7] .......................... A61K 31/19; A61K 31/34
(52) U.S. Cl. ......................... 514/461; 514/572
(58) Field of Search .................. 514/461, 572

(56) References Cited

U.S. PATENT DOCUMENTS

| 3,320,133 A |   | 5/1967 | Suga et al. |         |
|-------------|---|--------|-------------|---------|
| 5,387,605 A | * | 2/1995 | Beilfuss et al. | 514/461 |
| 5,824,326 A | * | 10/1998 | Grotty et al. | 424/401 |

FOREIGN PATENT DOCUMENTS

| EP | 582 359 | 2/1994 | ......... A01N/43/08 |
| EP | 801945 | 10/1997 | ............ A61K/7/48 |
| FR | 2 258 836 | 8/1975 | |
| JP | 59 067211 | 4/1984 | ............ A61K/7/00 |
| JP | 06 256137 | 9/1994 | ............ A61K/7/00 |

OTHER PUBLICATIONS

Action of Ferulic Acid and its Derivatives as Antioxidants, Kunio Yagi and Nobuko Ohishi, J. Nutr. Sci. Vitaminol., 25, 127–130, 1979.
The Multiactive Efficacy of Ferulic Acid in Cosmetics, Dr. Heinz Eggensperger, Chematic Consulting.
Hamburg, Michele Wilker, GfN GmbH, Wald Michelbach.
Antioxidant Potential of Ferulic Acid, Ernst Graf, Free Radical BViology & Medicine, vol. 13, pp. 135–148 1992.
The Multiactive Efficacy of Ferulic Acid and its Esters in Cosmetics, Dr. Heinz Eggensperger, Michele Wilker.
Vanllin as an Antimicrobial for Producing Shelf–Stable Strawberry Puree Patricia Cerrutti, Stella M. Alzamonia, and Susana L. Vidales—J. of Food Science, vol. 62, No. 3, 1997.
Chemical Abstracts, vol. 92, No. 23 published Jun. 9, 1980; abstract No. 92:198185 "Use Of Peroxide Oxidation of Furan Aldehydes . . . " Krapivin et al.
"Study Of Antibacterial And Antiinflammatory Components Of Achillea Alpina" Journal Of Traditional Chinese Medicine, vol. 3, No. 3 published 1983, pp. 213–216 Meilan et al.
Chemical Abstracts, vol. 104, No. 11 published Mar. 17, 1986, abstract No. 104:81532 "Pharmacological Effect Of The Organic Acids Of Achillea Alpina" Li et al.

\* cited by examiner

*Primary Examiner*—Zohreh Fay
(74) *Attorney, Agent, or Firm*—Karen A. Lowney, Esq.

(57) ABSTRACT

The present invention relates to cosmetic or pharmaceutical formulations for topical application which comprises an anti-inflammatory effective amount of 3-furan carboxylic acid. The formulation also optionally comprises an anti-irritant effective amount of frulic acid and an antimicrobial effective 2-furan carboxylic acid.

12 Claims, 3 Drawing Sheets

ANTIMICROBIAL COSMETIC COMPOSITIONS

RELATED APPLICATION

This application is a continuation in part of U.S. Ser. No. 08/896,194, filed Jul. 17, 1997, now U.S. Pat. No. 6,114,377 the contents of which are incorporated herein by reference.

FIELD OF THE INVENTION

The invention relates to novel cosmetic compositions. In particular, the invention relates to cosmetic compositions having unique antimicrobial and antiirritant properties.

BACKGROUND OF THE INVENTION

Water miscible cosmetic and toiletry formulations are frequently susceptible to microbial contamination, due to their high water content and the nature of ingredients that they often contain. This is particularly true with the trend toward "natural" cosmetic ingredients, which are more likely to be susceptible to contamination than synthetic ingredients may be. The occurrence of microbial contamination in a cosmetic formulation can result in an unpleasant odor or the destabilization of an emulsion; this in turn can lead to the necessity of reformulation or recall of a commercial product.

To counteract this problem, it is often necessary to add antimicrobial chemicals, such as preservatives or biocides, to the formulation to prevent the growth of microbes that may be introduced during the manufacturing, filling or use of the product. However, such additives have recently fallen into disfavor, in large part because many preservatives are perceived as causing irritation and consumers are now demanding preservative-free products. Therefore, the market is shifting toward lower levels of conventional preservatives, and also the replacement of conventional preservatives with new molecules. Thus, there is now a strong demand for cosmetic formulations which are non-irritating and free of traditional preservatives, but which will remain stable and free of contamination in the hands of the consumer. The present invention provides such formulations.

SUMMARY OF THE INVENTION

The present invention relates to a cosmetic or pharmaceutical formulation for topical application which comprises an antimicrobial effective amount of 3-furan carboxylic acid. In a preferred embodiment, the formulation also comprises an anti-irritant effective amount of ferulic acid, or a derivative thereof. In a particularly preferred embodiment, the formulation also comprises an antimicrobial effective amount of 2-furan carboxylic acid. All such formulations are capable of being made free of preservatives, and achieve the desired effects by the use of naturally occurring materials.

The invention also relates to method for reducing the irritant effect of a cosmetic or pharmaceutical formulation comprising adding to the formulation an anti-irritant effective amount of ferulic acid or a derivative or analog thereof, as well as reducing or preventing irritation on the skin by topical application to the skin of a formulation containing ferulic acid or a derivative thereof. The invention further relates to a method for reducing or preventing inflammation which comprises applying to the skin an anti-inflammatory effective amount of 2-furan carboxylic acid, 3-furan carboxylic acid, or a combination thereof. Also encompassed is a method for inhibiting microbial growth in a cosmetic or pharmaceutical formulation which comprises adding to the formulation an antimicrobial effective amount of 3-furan carboxylic acid.

Also provided by the invention are topical cosmetic and pharmaceutical compositions useful in the treatment of inflammation in the skin comprising effective amounts of 2-furan carboxylic acid, 3-furan carboxylic acid, or a mixture thereof, as well as methods of treating inflammatory reactions in the skin comprising applying such compositions to the skin.

DETAILED DESCRIPTION OF THE INVENTION

Figure 1A:
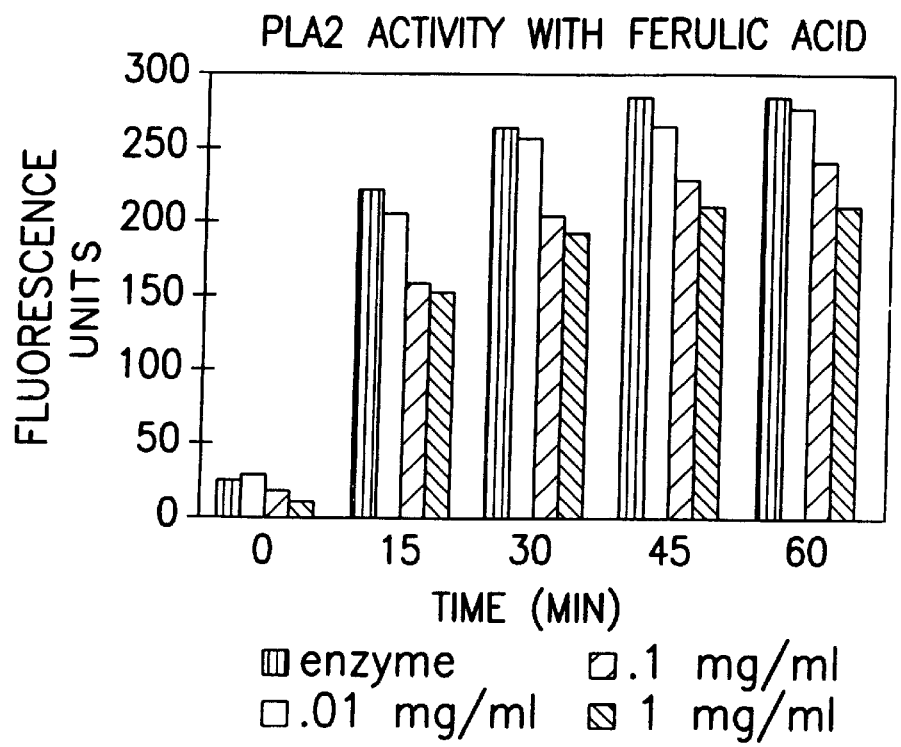
FIG. 1 illustrates the inhibitory effect of (A)ferulic acid; (B)2-furan carboxylic(2-furoic) acid; and (C)3-furan carboxylic(3-furoic) acid on phospholipase $A_2$ activity.

Furan carboxylic acids are naturally occurring degradation products from lignin and cellulose. 2-furan carboxylic acid has previously been disclosed as having antimicrobial activity, and has been said to be particularly effective against mycobacteria (U.S. Pat. No. 5,387,605). However, antimicrobial activity for 3-furan carboxylic acid has not previously been reported; in the context of the present invention, it has now been unexpectedly discovered that 3-furan carboxylic acid has potent antimicrobial properties. Particularly surprising is the observation that this acid has a greater level of antimicrobial activity than 2-furan carboxylic acid. In contrast with the latter, 3-furan carboxylic acid has sufficient antimicrobial activity to be used as the sole antimicrobial in a cosmetic formulation over a broad pH range. In particular, it is noted that 3-furan carboxylic acid is capable of preventing growth of Enterics, Pseudomonas, Staphylococcus and Mold, and substantially reducing the growth of yeast; in contrast, although 2-furan carboxylic acid does exhibit inhibition of Enterics, Pseudomonas, and Staphylococcus, it has a very poor level of activity against Mold and yeast, making it inadequate on its own to preserve a cosmetic formulation. To achieve the desired antimicrobial effect, 3-furan carboxylic acid alone can be used in the formulation in an amount of from about 0.05–5%, preferably 0.1–3%, by weight of the total composition. Although the 2-furan carboxylic acid alone is insufficient protection, it may be desirable to use it in combination with 3-furan carboxylic acid as a supplement to that acid's activity, in an amount of 0.5–5%. In preferred formulations of the invention, both acids are combined, and in each case, throughout the specification and the claims, when the acid is referred to, it is understood that this refers to both the free acid and derivatives thereof having the same activity. These compounds are available commercially, for example, from Sigma Chemical.

It has also been observed that both 2- and 3-furan carboxylic acids possess a surprising level of anti-inflammatory activity. When tested in standard in vitro assays for anti-inflammatory activity, both compounds have been shown to be potent inhibitors of one or more steps in the inflammatory cascade. Both 2- and 3-furan carboxylic exhibit the ability to inhibit the adhesion of polymorphonuclear leukocytes (PMNs) to activated endothelial cells, an indicator of chronic, rather than acute, inflammation. In addition, both compounds are capable of inhibiting the activity of Phospholipase $A_2$ enzyme, which is a stimulator of arachidonic acid production; this is an indicator of inhibition of one of the early events in the inflammatory cascade of events, indicating an ability to inhibit acute inflammatory responses. In this particular property, however, 3-furan carboxylic acid is exceptionally active, inhibiting activity at a level of 0.01 mg/ml. Therefore, in an additional embodiment of the invention, a cosmetic or pharmaceutical composition for treatment or prevention of inflammation is provided, the composition comprising from anti-inflammatory effective amounts of 2-furan carboxylic acid, 3-furan carboxylic acid, or a mixture thereof. Generally speaking, the effective amounts of these compounds will be in the same range as required for their antimicrobial activity. Such compositions are useful in the treatment and prevention of skin conditions or disorders which comprise an inflammatory aspect, for example, psoriasis, eczema, allergic contact dermatitis, or atopic dermatitis.

An additional useful component of the formulation is ferulic acid or derivatives thereof. Ferulic acid is also a naturally occurring material; it is found as a free acid in plants, and also occurs in ester form in seeds, leave and bark of plants. Esters are formed, for example, with long chain alcohols, sterols, and hydroxyacids. Ferulic acid has previously been said to exhibit a variety of biological activities, such as antioxidant, deodorant, antiinflammatory, antimicrobial and antipruritic. It has not, however, to the inventors' knowledge, been identified as an antiirritant. In accordance with the present invention, ferulic acid has been shown to have substantial antiirritant properties, which render it particularly useful in cosmetic formulations, and may be particularly desirable in combination with an active acid component that has the potential of causing irritation on the skin. The antiirritant effect of ferulic acid can be achieved by application shortly prior to, or simultaneously with, or shortly after exposure of the skin to an irritating material. It may also be used alone to generally soothe sensitive, easily irritated skin. As used herein, the term "ferulic acid" will be understood to encompass both the free acid and ester forms having the same activity as the free acid, unless otherwise specified. In the formulation, the ferulic acid is preferably used in an amount of from about 0.05–2.5%, more preferably 0.1–1% by weight of the total composition.

It is particularly preferred that ferulic acid, or an ester thereof, is combined with both 2-furan carboxylic acid and 3-furan carboxylic acid, in the amounts specified above for each individual component. The formulations containing this combination exhibit sufficient antimicrobial control to avoid the use of conventional cosmetic or pharmaceutical preservatives. By "conventional" preservatives is meant those preservatives which have been routinely used in the past for inhibition of microbial growth; these include, but are not limited to, parabens, propionates, formaldehyde releasers, benzoates, and cresols. An added advantage of such formulations is that they are not only inherently non-irritating, but also reduce irritation already existing on the skin to which they are applied.

In an optional embodiment, the formulations may also comprise vanillin, vanillic acid, or vanillic acid esters, in an amount of from about 0.05–1%. Vanillin is also a naturally occurring material, which is known to have activity as an antimicrobial (Principles and Practice of Disinfection, Preservation and Sterilization, Russell et al, eds., Second Edition, Blackwell Scientific Publications; Cerrutti et al., J. Food Sci. 62: 608–610, 1997.)

For topical application, the active components can be formulated with a variety of cosmetically and/or pharmaceutically acceptable carriers. The term "pharmaceutically or cosmetically acceptable carrier" refers to a vehicle, for either pharmaceutical or cosmetic use, which vehicle delivers the active components to the intended target and which will not cause harm to humans or other recipient organisms. As used herein, "pharmaceutical" or "cosmetic" will be understood to encompass both human and animal pharmaceuticals or cosmetics. Useful carriers include, for example, water, acetone, ethanol, ethylene glycol, propylene glycol, butane-1,3-diol, isopropyl myristate, isopropyl palmitate, or mineral oil. Methodology and components for formulation of cosmetic and pharmaceutical compositions are well known, and can be found, for example, in Remington's Pharmaceutical Sciences, Eighteenth Edition, A. R. Gennaro, Ed., Mack Publishing Co. Easton Pennsylvania, 1990. The carrier may be in any form appropriate to the mode of delivery, for example, solutions, colloidal dispersions, emulsions(oil-in-water or water-in-oil), suspensions, creams, lotions, gels, foams, mousses, sprays and the like. The pH for the formulations of the invention can be from about 3 to about 8, preferably about 4–7, and most preferably about 4–6.

The formulation, in addition to the carrier and the antimicrobial/antiirritant components, also can comprise other optional materials which may be chosen depending on the carrier and/or the intended use of the formulation. Additional components include, but are not limited to, water soluble colorants (such as FD&C Blue #1); oil soluble colorants (such as D&C Green #6); water soluble sunscreens (such as Eusolex 232); oil soluble sunscreens (such as Octyl Methoxycinnamate); particulate sunscreens (such as Zinc Oxide); antioxidants (such as BHT); chelating agents (such as Disodium EDTA); emulsion stabilizers (such as carbomer); preservatives (such as Methyl Paraben); fragrances (such as pinene); flavoring agents (such as sorbitol); humectants (such as glycerine); waterproofing agents (such as PVP/Eicosene Copolymer); water soluble film-formers (such as Hydroxypropyl methylcellulose); oil-soluble film formers (such as Hydrogenated C-9 Resin); cationic polymers (such as Polyquaternium 10); anionic polymers (such as xanthan gum); vitamins (such as Tocopherol); and the like.

The antimicrobial/antiirritant/antiinflammatory components are well-suited for combination with other active components intended for topical application. In particular, the ferulic acid may assist in reducing the irritating effects of other active components in a formulation. Examples of known irritants that are frequently used for therapeutic purposes topically are retinoids, such as retinol and retinoic acid, and hydroxyacids, such as glycolic, lactic, or salicylic acids. Examples of other types of actives which may form part of the composition include, but are not limited to, those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antpsoriatic agents, antiseborrheic agents, hair conditioners and hair treatment agents, antiaging agents, antiwrinkle agents, antiasthmatic agents and bronchodilators, sunscreen agents, antihistamine agents, skin lightening agents, depigmenting agents, wound-healing agents, vitamins, corticosteroids, tanning agents, sunscreens or hormones. More specific examples of useful active agents include retinoids, topical cardiovascular agents, clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, retinol, retinoic acid, 13-cis retinoic acid, hydrocortisone, hydrocortisone 21-acetate, hydrocortisone 17-valerate, hydrocortisone 17-butyrate, betamethasone valerate, betamethasone diproprionate, triamcinolone acetonide, fluocinonide, clobetasol, proprionate, benzoyl peroxide, crotamiton, propranolol, promethazine, vitamin A palmitate, vitamin E acetate, DHEA and derivatives thereof, alpha- or beta-hydroxy acids, and mixtures thereof. The amount of active agent to be used in any given formulation is readily determined in accordance with its usual dosage.

Particularly preferred embodiments of the present formulations are moisturizing creams or lotions. To that end, the antimicrobials/antiirritant components are combined with agents that are moisturizers, emollients or humectants. Examples of useful combinations are oils, fats, waxes, esters, fatty acid alcohols, fatty acid ethoxylates, glycols, sugars, hyaluronic acid and hyaluronates, dimethicone, cyclomethicone, and the like. Further examples can be found in the International Cosmetic Ingredient Dictionary, CTFA, Sixth Edition, 1995.

The invention is further illustrated by the following non-limiting examples.

Application of the formulations of the invention is achieved in accordance with the nature and intended use of the final product. For example, a moisturizing, cleansing, or skin-soothing formulation may be used on a daily basis, or more or less frequently depending upon need. If the formulation contains a pharmaceutical or cosmetic active, the application will be in accordance with the recommended regimen for the active. Determination of other appropriate application regimens is a matter of routine optimization.

EXAMPLES

I. This example illustrates the efficacy of 3-furan carboxylic acid in retarding microbial growth in a cosmetic formulation.

A nonionic oil-in-water emulsion is prepared containing 0.473% 3-furan carboxylic acid. The formulation is divided into five portions, each one getting an inoculation at day 0, and a reinoculation after three weeks, of one of the following microbial cultures: (1)Enterics; (2) Pseudomonas; (3)Staphylococcus; (4)Yeast; and (5)Mold. The concentration of microbes in each individual formulation is calculated on the day of the inoculation, and then again calculated on day 2, and at the end of one, two, three (pre-reinoculation) and four weeks, at a variety of pH values. These are also compared with formulations containing 2-furan carboxylic acid and an identical series of microbes, and an acid pH control emulsion without a furan carboxylic acid added. The results are shown in Tables 1, 2 and 3. All numbers, other than those listed as "<10", are log base 10; thus, for example, "6.6" is equivalent to the presence of 8 million bacteria. Entries of <10 indicate less than 10 colony forming units, the lowest level of detection.

TABLE 1

0.473% 3-furan carboxylic acid

| Pool # | Day 0 | Day 2 | Week 1 | Week 2 | Week 3 | Week 4 |
|---|---|---|---|---|---|---|
| A. pH 3.0 | | | | | | |
| 1 | 6.6 | <10 | <10 | <10 | <10 | <10 |
| 2 | 6.3 | <10 | <10 | <10 | <10 | <10 |
| 3 | 6.3 | <10 | <10 | <10 | <10 | <10 |
| 4 | 5.7 | <10 | <10 | <10 | <10 | <10 |
| 5 | 5.2 | <10 | <10 | <10 | <10 | <10 |
| B. pH 4.0 | | | | | | |
| 1 | 6.6 | <10 | <10 | <10 | <10 | <10 |
| 2 | 6.3 | <10 | <10 | <10 | <10 | <10 |
| 3 | 6.3 | <10 | <10 | <10 | <10 | <10 |
| 4 | 5.7 | 2.5 | <10 | <10 | <10 | <10 |
| 5 | 5.2 | <10 | <10 | <10 | <10 | <10 |
| C. pH 5.0 | | | | | | |
| 1 | 6.6 | <10 | <10 | <10 | <10 | <10 |
| 2 | 6.3 | <10 | <10 | <10 | <10 | <10 |
| 3 | 6.3 | <10 | <10 | <10 | <10 | <10 |
| 4 | 5.7 | 2.5 | 2.7 | 1.7 | 2.0 | 1.8 |
| 5 | 5.2 | <10 | <10 | <10 | <10 | <10 |

TABLE 2

0.375% 2-furan carboxylic acid

| Pool # | Day 0 | Day 2 | Week 1 | Week 2 | Week 3 | Week 4 |
|---|---|---|---|---|---|---|
| A. pH 3.0 | | | | | | |
| 1 | 6.6 | <10 | <10 | <10 | <10 | <10 |
| 2 | 6.3 | <10 | <10 | <10 | <10 | <10 |
| 3 | 6.3 | <10 | <10 | <10 | <10 | <10 |
| 4 | 5.7 | <10 | <10 | <10 | <10 | <10 |
| 5 | 5.2 | <10 | <10 | <10 | <10 | <10 |
| B. pH 4.0 | | | | | | |
| 1 | 6.6 | <10 | <10 | <10 | <10 | <10 |
| 2 | 6.3 | <10 | <10 | <10 | <10 | <10 |
| 3 | 6.3 | <10 | <10 | <10 | <10 | <10 |
| 4 | 5.7 | 3.7 | 3.7 | <10 | <10 | >5.7 |
| 5 | 5.2 | 1.6 | <10 | <10 | <10 | <10 |
| C. pH 5.0 | | | | | | |
| 1 | 6.6 | >6 | >6 | <10 | <10 | <10 |
| 2 | 6.3 | >6 | <10 | <10 | <10 | <10 |
| 3 | 6.3 | 2.9 | <10 | <10 | <10 | <10 |
| 4 | 5.7 | >5.7 | >5.7 | >5.7 | >5.7 | >5.7 |
| 5 | 5.2 | 5.2 | 5.2 | 5.2 | 3.0 | >5 |

TABLE 3

Control emulsion

| Pool # | Day 0 | Day 2 | Week 1 | Week 2 | Week 3 | Week 4 |
|---|---|---|---|---|---|---|
| A. pH 3.0 | | | | | | |
| 1 | 6.6 | 3.7 | <10 | <10 | <10 | <10 |
| 2 | 6.3 | >6 | <10 | <10 | <10 | <10 |
| 3 | 6.3 | 2.0 | <10 | <10 | <10 | <10 |
| 4 | 5.7 | 5.7 | 5.7 | 5.7 | 4.5 | >6 |
| 5 | 5.2 | 5.2 | 5.2 | 5.2 | 5.2 | >5 |
| B. pH 4.0 | | | | | | |
| 1 | 6.6 | >6 | >6 | 3.2 | <10 | >6 |
| 2 | 6.3 | >6 | >6 | <10 | <10 | <10 |
| 3 | 6.3 | >6 | 2.0 | 2.0 | <10 | <10 |
| 4 | 5.7 | >6 | >6 | >6 | >6 | >6 |
| 5 | 5.2 | 5.2 | 5.2 | 5.2 | 3.3 | >5 |
| C. pH 5.0 | | | | | | |
| 1 | 6.6 | >6 | >6 | >6 | 2.0 | >6 |
| 2 | 6.3 | >6 | >6 | <10 | <10 | <10 |

TABLE 3-continued

| | | Control emulsion | | | | |
|---|---|---|---|---|---|---|
| Pool # | Day 0 | Day 2 | Week 1 | Week 2 | Week 3 | Week 4 |
| 3 | 6.3 | >6 | >6 | >6 | 4.2 | <10 |
| 4 | 5.7 | >6 | >6 | >6 | >6 | >6 |
| 5 | 5.2 | >5.2 | 5.2 | 5.2 | 3.0 | >6 |

Comparison of the antimicrobial effects of the two furan carboxylic acids shows that the 3-furan carboxylic acid is superior to 2-furan carboxylic acid in its ability to retard the growth of mold and yeast. The control shows that the antimicrobial effect of these two acids is due to the characteristics of the specific acid, rather than the acid pH or the vehicle used.

Example 2

This example illustrates the antiirritant effect of the components of the invention Seven volunteers with a history of skin sensitivity to Balsam of Peru are chosen for the study. The test compounds studied are as follows: Ferulic acid, 0.1% in hydroalcohol 1:1; 2-furan carboxylic acid, 0.1% in hydroalcohol 1:1; and 3-furan carboxylic acid, 0.1% in hydroalcohol, 1:1.

The test compounds are applied to the ventral forearms of panelists. The material is allowed to absorb for twenty minutes and then Balsam of Peru, an irritant is applied on the test sites. Skin irritation is measured in terms of increase in skin redness. The degree of redness is measured with a Minolta Chromameter and compared with the controls, the positive control being skin treated with Balsam of Peru alone, and the negative control being a skin site treated with 10% cola solution(a known antiirritant), and challenged like the test products.

Ferulic acid is 72% effective in preventing the onset of irritation. This compares favorably with the cola solution, which shows 69% reduction. Interestingly, both 2- and 3-furan carboxylic acid show some reduction in the onset of irritation, at 49% and 48%, respectively.

Example 3

This example illustrates the anti-inflammatory effect of 2- and 3-furan carboxylic acids, in two different aspects of the inflammatory cascade.

A. $PLA_2$ (phospholipase $A_2$)inhibition

The enzyme reaction is accomplished in a cuvette containing 2 m of phosphate buffered saline. Fluorometric substrate NBD-C6-HPC is solubilized 1 mM in EtOH, and is diluted in the reaction mixture to yield a 10 μM final concentration. The assay is initiated with the addition of 0.001 units per μl of $PLA_2$ enzyme obtained from snake venom. Enzyme activity is monitored either with or without the presence of potential inhibitors. Materials tested are solubilized as follows: ferulic acid and 2-furan carboxylic acid are solubilized 10 mg/ml in EtOH, and 3-furan carboxylic acid is solubilized 100 mg/ml in EtOH; each sample is diluted appropriately to yield assay concentrations of 0.01, 0.1 and 1 mg/ml. Prior to enzyme addition, samples are measured fluorometrically at excitation 470 and emission 570 to determine background level of fluorescensce. Following enzyme addition, samples are monitored every 15 minutes over a 60 minute period.

Figure 1B:
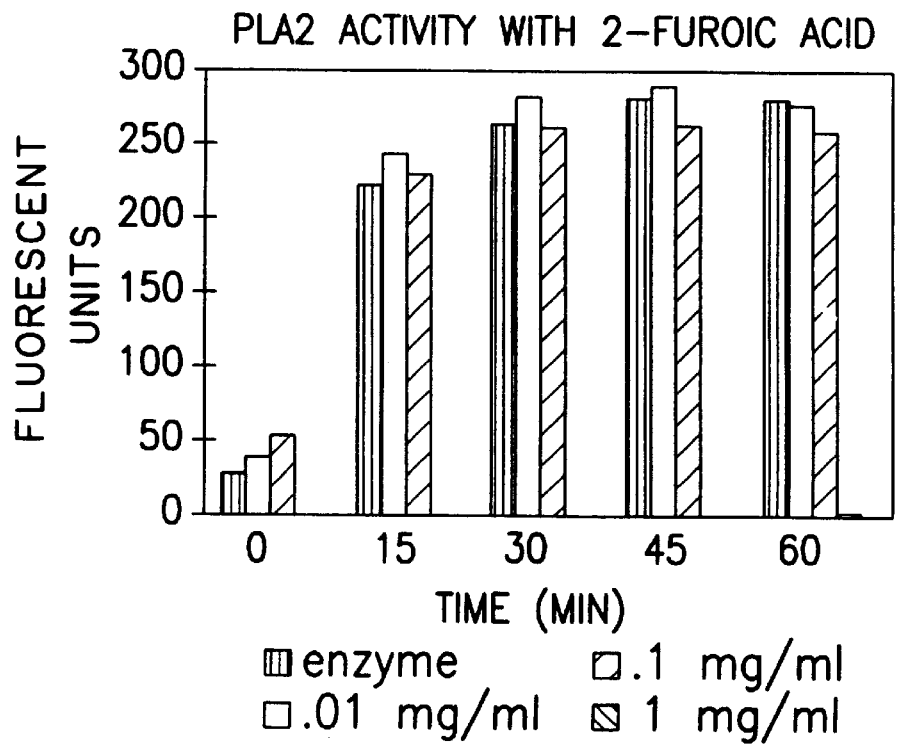
Figure 1C:
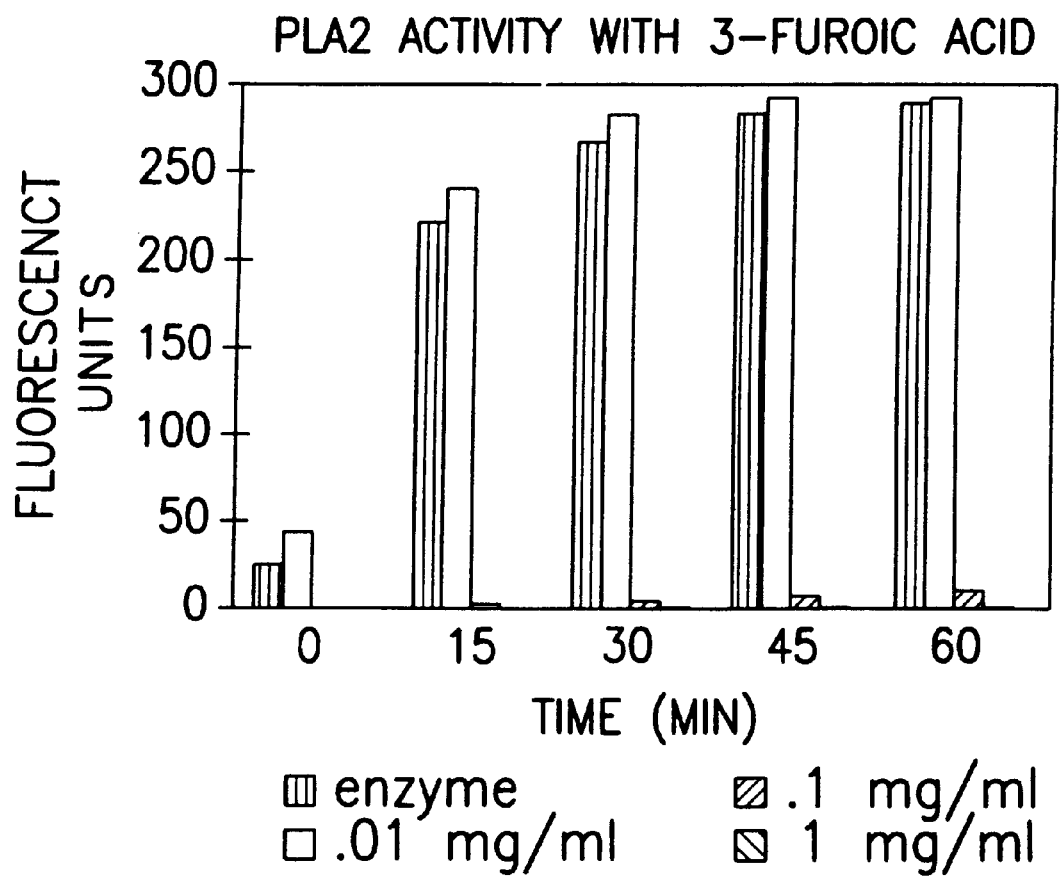

EC-50 values are calculated, but are limited to those samples which best yield a linear fit. Of those calculable in this manner, 2-furan carboxylic acid yielded a 0.5 mg/ml value (FIG. 1a). Although it was not possible to calculate an EC-50 for 3-furan carboxylic acid, as shown in FIG. 1b, it provides the greatest inhibition by blocking the enzyme activity at 0.1 mg/ml dose. Ferulic acid also shows some inhibitory effect, but is the weakest of the three tested (FIG. 1c).

B. Inhibition of lymphocyte adhesion

Endothelial cells are grown to confluence and washed thoroughly with basal media prior to the experiment to remove all fetal calf serum. The test compounds are then added to the endothelial culture well and incubated for 2 hours. IL-1β is added to stimulated expression of adhesion molecules on the endothelial cells before lymphocytes are added.

Lymphocytes are isolated from blood collected from adult human subjects and added to the endothelial culture wells. PHA is added to stimulate adhesion molecule expression in the lymphocytes and the cultures incubated overnight. After a brief washing procedure, cells are incubated with Rose Bengal, and the number of adherent cells assessed by measuring the absorbance at 570 nm.

Figure 2:
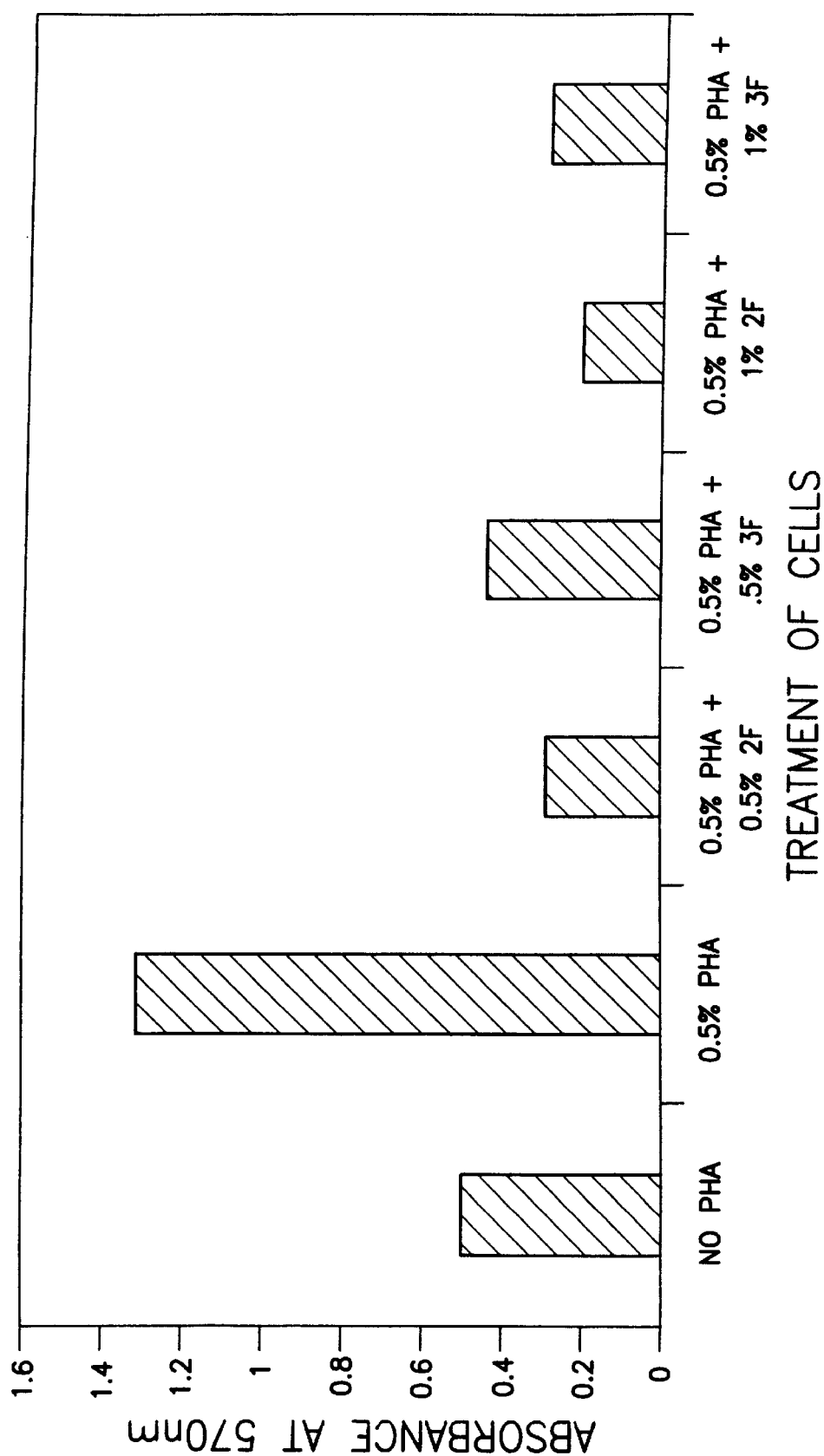
FIG. 2 illustrates the inhibitory effect of 2-furan carboxylic acid(2F) and 3-furan carboxylic acid (3F) on the inhibition of lymphocyte adhesion to endothelial cells.

FIG. 2 illustrates that both 2- and 3-furan carboxylic acid are very potent inhibitors of lymphocyte adhesion at concentrations of 0.5% and 1%. The first bar shows the absorbence of endothelial cells plus any adherent lymphocytes under non-stimulated conditions. The second shows the increase in absorbance after overnight incubation with PHA. The next four bars show the decrease in absorbance back to non-stimulated conditions in cultures preincubated with either 0.5% or 1% of the two acids.

What we claim is:

1. A cosmetic or pharmaceutical formulation for topical application comprising an antiirritant effective amount of ferulic acid, in combination with an irritating active component.

2. The formulation of claim 1 which also comprises an antimicrobial effective amount of 2-furan carboxylic acid and 3-furan carboxylic acid.

3. A method of inhibiting inflammation in the skin which comprises applying to the skin an effective amount of 3-furan carboxylic acid.

4. The method of claim 3 which comprises applying 2-furan carboxylic acid in combination with 3-furan carboxylic acid.

5. The method of claim 3 in which ferulic acid is also applied.

6. The method of claim 5 which comprises applying free 2-furan carboxylic acid, free 3-furan carboxylic acid, and free ferulic acid.

7. A method of treating a skin disorder having an inflammatory component comprising applying to the skin an effective amount of 2-furan carboxylic acid, 3-furan carboxylic acid, or a mixture thereof.

8. The method of claim 7 in which the skin disorder is selected from the group consisting of psoriasis, eczema, allergic contact dermatitis, or atopic dermatitis.

9. The method of claim 7 which comprises applying free 3-furan carboxylic acid.

10. The method of claim 7 which comprises applying free 2-furan carboxylic acid.

11. The method of claim 7 in which free ferulic acid is also applied.

12. The method of claim 7 which comprises applying free 2-furan carboxylic acid, free 3-furan carboxylic acid, and free ferulic acid.

* * * * *